United States Patent [19]

Imai et al.

[11] Patent Number: 4,774,346

[45] Date of Patent: Sep. 27, 1988

[54] METHOD FOR PURIFYING HEXAMETHYLDISILOXANE

[75] Inventors: Takeshi Imai; Masahiko Suzuki; Ikuzo Takahashi; Shuzo Toida, all of Chiba, Japan

[73] Assignee: Toray Silicone Co., Ltd., Tokyo, Japan

[21] Appl. No.: 148,414

[22] Filed: Jan. 26, 1988

[30] Foreign Application Priority Data

Feb. 3, 1987 [JP]  Japan ................................. 62-23325

[51] Int. Cl.$^4$ ................................................. C07F 7/08
[52] U.S. Cl. ..................................................... 556/456
[58] Field of Search .......................................... 556/456

[56] References Cited

U.S. PATENT DOCUMENTS

| | | | |
|---|---|---|---|
| 3,493,595 | 2/1970 | Strasser et al. | 556/456 X |
| 4,127,598 | 11/1978 | McEntee | 556/456 X |
| 4,156,689 | 5/1979 | Ashby et al. | 260/448.2 |
| 4,210,496 | 7/1980 | Wong | 203/46 |
| 4,370,204 | 1/1983 | Kotzsch et al. | 203/39 |
| 4,661,612 | 4/1987 | George et al. | 556/456 X |

FOREIGN PATENT DOCUMENTS 59-209565 10/1984 Japan ........................ 556/456 UX

*Primary Examiner*—Paul F. Shaver
*Attorney, Agent, or Firm*—Carl A. Yorimoto

[57] ABSTRACT

A method for purifying impure hexamethyldisiloxane comprising as a major portion hexamethyldisiloxane and as a minor portion a mixture of low-boiling organic solvents, other organosilicon compounds, and odor-producing materials is described. The method comprises (A) first, treating the impure hexamethyldisiloxane with a condensation catalyst to convert the organosilicon compounds to additional hexamethyldisiloxane; (B) second, washing the treated impure hexamethyldisiloxane with water; (C) third, separating a water phase from the washed impure hexamethyldisiloxane; (D) fourth, distilling the washed impure hexamethyldisiloxane to yield hexamethyldisiloxane of enhanced purity; (E) fifth, contacting the hexamethyldisiloxane of enhanced purity with acid clay at a temperature of greater than about 50° C.; and (F) finally, contacting the acid clay treated hexamethyldisiloxane of enhanced purity treated in (E) with activated carbon to yield hexamethyldisiloxane with enhanced purity and minimal unpleasant odor.

13 Claims, No Drawings

METHOD FOR PURIFYING HEXAMETHYLDISILOXANE

BACKGROUND OF THE INVENTION

The instant invention relates to a method for purifying hexamethyldisiloxane. More specifically the instant invention relates to a purification method which affords a very pure hexamethyldisiloxane, lacking any unpleasant smell, from the very impure hexamethyldisiloxane ultimately recovered from the trimethylchlorosilane and hexamethyldisilazane used as silylating agents in the pharmaceutical industry.

Trimethylchlorosilane and hexamethyldisilazane are widely used as silylating agents in the pharmaceutical manufacturing industry, such as in the production of antibiotics such as penicillin cephalosporin, etc. The hexamethyldisiloxane produced and recovered as a by-product from this trimethylchlorosilane or hexamethyldisilazane contains large quantities of impurities. such as organic solvents, since the silyl group protective reaction is conducted in the presence of a low-boiling organic solvent, as well as trimethylsilanol, trimethylmethoxysilane, etc.

Hexamethyldisiloxane no longer functions as a silylating agent for pharmaceutical manufacture. Also, it is technically difficult to obtain a very pure, deodorized hexamethyldisiloxane from the very impure hexamethyldisiloxane recovery liquid. The primary method of handling this recovery liquid is the distillative recovery of a major part of the organic solvent, with the residue being incinerated as an industrial waste. Even when the hexamethyldisiloxane is recovered, it has a distinctly unpleasant odor which limits its use.

SUMMARY OF THE INVENTION

The object of the instant invention is to provide a purification method which affords a very pure, deodorized hexamethyldisiloxane from the highly impure hexamethyldisiloxane recovery liquid generated as a by-product in the silylation reaction. It is difficult to obtain a deodorized hexamethyldisiloxane from this recovery liquid by distillation only. The instant invention is a purification method which affords a very pure, deodorized hexamethyldisiloxane in high yields by virtue of the incorporation of relatively simple processes. As a consequence, the hexamethyldisiloxane can be used as a plasticizer in the manufacture of silicone rubbers, as a starting material in the preparation of silicone compounds, as an agent imparting water resistance to inorganic materials, etc.

The object of the instant invention can be achieved by a method for purifying hexamethyldisiloxane which is characterized in that an acidic or basic compound is added to the highly impure hexamethyldisiloxane. The impurities are, in part, condensed or hydrolytically condensed at room temperature or with heating. This treatment is followed by a wash with water and distillation to afford a hexamethyldisiloxane of enhanced purity. This hexamethyldisiloxane is then heat treated with acid clay and subsequently brought into contact with activated carbon.

A very impure hexamethyldisiloxane is recovered in the pharmaceutical sector as a by-product from silylation using trimethylchlorosilane or hexamethyldisilazane; however, even after distillation this hexamethyldisiloxane continues to have a distinctly unpleasant smell, which is caused by impurities. As a consequence, its use in the typical applications of hexamethyldisiloxane is avoided. In the instant inventions method of hexamethyldisiloxane purification, the yield is substantially improved because distillation is carried out after monofunctional triorganosilane impurities in the hexamethyldisiloxane recovery liquid have been converted into hexamethyldisiloxane by condensation or hydrolytic condensation. Furthermore, the instant invention also has the effect of completely eliminating the disagreeable odor through the joint application of an acid clay treatment and activated carbon treatment after distillation.

As a consequence, a very pure, deodorized hexamethyldisiloxane is readily produced in high yields, and it can be used in the typical applications known in the art for hexamethyldisiloxane. Thus, it can be efficiently utilized in the industry, making the invention very beneficial to the industry.

DESCRIPTION OF THE INVENTION

In accordance with the instant invention there is provided a method for purifying hexamethyldisiloxane under conditions that will be delineated herein. What is described, therefore, is a method for purifying impure hexamethyldisiloxane comprising as a major portion hexamethyldisiloxane and as a minor portion a mixture of low- boiling organic solvents, other organosilicon compounds, and odor-producing materials, said method comprising (A) first, treating the impure hexamethyldisiloxane with a condensation catalyst to convert the other organosilicon compounds to additional hexamethyldisiloxane;

(B) second, washing the treated impure hexamethyldisiloxane from (A) with water;

(C) third, separating a water phase from the washed, treated impure hexamethyldisiloxane;

(D) fourth, distilling the washed, treated impure hexamethyldisiloxane to yield hexamethyldisiloxane of enhanced purity;

(E) fifth, contacting the hexamethyldisiloxane of enhanced purity with acid clay at a temperature of greater than about 50° C.; and (F) finally, contacting the hexamethyldisiloxane of enhanced purity treated in (E) with activated carbon.

The hexamethyldisiloxane recovery liquid generated as a by-product from the silylation reaction contains large amounts of impurities in the form of low-boiling organic solvent such as, for example, acetone, dichloromethane, methanol, dioxane, isopropanol, or tetrahydrofuran, etc., as well as other organosilicon compounds such as, for example trimethylsilanol, trimethylmethoxysilane, etc. The instant invention seeks to improve the yield by means of the addition, prior to distillation of the recovery liquid, of a catalyst (an acidic compound or a basic compound) with subsequent conversion of impurities such as trimethylsilanol, trimethylmethoxysilane, etc., into hexamethyldisiloxane by a condensation or hydrolytic condensation at room temperature or with heating.

The condensation catalysts used here are organic or inorganic acidic or basic compounds such as, for example, hydrochloric acid, sulfuric acid, acetic acid, paratoluenesulfonic acid, sodium hydroxide, potassium hydroxide, or organic amines. The condensation catalyst is added at between 0.01 to 1.0 weight percent based on the hexamethyldisiloxane recovery liquid, which is then subjected to condensation or hydrolytic condensation at temperatures between room temperature and 100° C. The simultaneous addition of water at this point provides for the smooth execution of the condensation and hydrolytic condensation reactions and an efficient conversion into the target hexamethyldisiloxane.

After completion of the condensation and hydrolytic condensation reactions, the liquid is neutralized by removing the catalyst by washing the liquid with water, using the latter at 1-fold to 10-fold based on the total quantity of the liquid. At this time, water-soluble solvents will transfer into the aqueous phase, but since hexamethyldisiloxane is almost insoluble in water, this water wash actually provides for the secondary separation of part of the solvent.

The water-washed hexamethyldisiloxane is then distilled in order to separate the remaining organic solvent and small quantities of high-boiling compounds. A packed rectification column can be used here, although this will depend on the nature of the organic solvent present in the hexamethyldisiloxane, and 50 or fewer plates will be satisfactory for the number of separation stages. Attempts to achieve distilled hexamethyldisiloxane purities of, for example, 99 weight percent or greater as the gas chromatographic value, will not encounter particular problems since this is merely a problem in the technique of distillation. For the purposes of the instant invention, the term "hexamethyldisiloxane of enhanced purity" refers to a distilled material significantly increased in hexamethyldisiloxane content from the impure hexamethyldisiloxane. That is, the hexamethyldisiloxane of enhanced purity can have a purity of 99 weight percent or better as compared to the purity of 50 to 60 weight percent of the impure hexamethyldisiloxane.

While the hexamethyldisiloxane obtained by carrying out the method up to this point has a satisfactory purity, the obtained hexamethyldisiloxane nonetheless has a distinctly unpleasant smell due to the presence of microquantities of impurities which cannot be removed by distillation. Thus, it cannot be used as such in the applications of a hexamethyldisiloxane synthesized by the usual method of hydrolytic condensation of trimethylchlorosilane, since the latter does not have this unpleasant smell.

Accordingly, the present inventors thoroughly examined the elimination of this unpleasant odor and found as a result that merely bringing this distilled hexamethyldisiloxane having a disagreeable odor into contact with activated carbon had little effect. However, it was found that the unpleasant smell could be completely eliminated by contact with activated carbon after a heat treatment with acid clay, thus affording a hexamethyldisiloxane having the fresh smell of a hexamethyldisiloxane manufactured by trimethylchlorosilane hydrolysis.

With regard to the conditions in the heat treatment of the bad smelling hexamethyldisiloxane with acid clay, the microquantities of impurities which are the sources of the odor can be liberated from the hexamethyldisiloxane by adding the acid clay at 0.01 to 10 weight percent based on hexamethyldisiloxane and heating to between 50° and 98° C. (the boiling point of hexamethyldisiloxane). An inert gas such as nitrogen can be injected into the reactor at this time, and in such a case part of the odor will be carried by the inert gas from the treatment reactor to the exterior.

After heat treatment with acid clay, the hexamethyldisiloxane is then brought into contact with activated carbon in order to completely remove the microquantities of liberated bad smelling compounds by adsorption. No specific restriction is placed on the activated carbon in this regard, and it can be granular or microparticulate. With regard to the procedure for contact with the activated carbon, 0.01 to 5 weight percent activated carbon (based on hexamethyldisiloxane) is added, mixing is carried out at room temperature to 100° C., and this is followed by filtration. Alternatively the hexamethyldisiloxane may be continuously passed through an activated carbon-packed column maintained in the above-mentioned temperature range. The second method is preferred since activated carbon present in the hexamethyldisiloxane can then be removed by simple filtration, for example, by a cartridge-type filter composed of glass fiber or plastic fiber.

The hexamethyldisiloxane produced as above is very pure, is colorless and transparent in its external appearance, and has the distinctive fresh odor of the hexamethyldisiloxane prepared by the hydrolysis of trimethylchlorosilane. Just as for the latter hexamethyldisiloxane, this former hexamethyldisiloxane can be effectively utilized as a plasticizer in the production of silicone rubbers, as a starting material in the production of silicone compounds, as an agent for treating inorganic materials to impart water resistance, etc.

So that those skilled in the art can better understand and appreciate the instant invention, the following examples are presented. The examples are presented to be illustrative and are not to be construed as limiting the claims of the instant invention. In the examples, %=wt% in all cases.

EXAMPLE 1

A solution recovered as the waste solution from sylation contained 56.3% hexamethyldisiloxane and 19.2% dichloromethane, 11.7% trimethylmethoxysilane, 12.2% trimethylsilanol, and 0.6% other as impurities. To 1,000 g of this solution were added 2 g concentrated hydrochloric acid and ion-exchanged water. After mixing for 2 hours at room temperature, the solution was washed 3 times with 1,500 ml ion-exchanged water to neutrality. The oil layer (890 g) was recovered, and contained 10.0% dichloromethane and 90.0% hexamethyldisiloxane. This liquid was placed in a 2 l distillation set-up (equipped with a 30 cm tall glass fractionation column packed with glass Raschig rings), and distilled under ambient pressure to obtain 620 g distillate with a boiling point of 99° C. This was hexamethyldisiloxane having a purity of 99.83% as measured by gas chromatography, but it had a distinctly unpleasant smell. 300 g of this hexamethyldisiloxane and 3 g acid clay (K-500 from Nippon Kassei Hakudo Kabushiki Kaisha) were placed in a 500 ml flask and stirred at between 90° and 100° C. for 8 hours. After cooling to room temperature, 5 g powdered coconut husk activated carbon (Kanto Kagaku Kabushiki Kaisha) was added. After mixing for 3 hours at room temperature, the liquid was then filtered on a glass filter. A colorless and transparent hexamethyldisiloxane with a characteristic fresh smell was obtained quantitatively with respect to the amount taken.

The bad smelling hexamethyldisiloxane obtained from distillation was also directly treated with the coconut husk activated carbon, omitting the heat treatment with acid clay but otherwise using the same conditions as above. In this case, absolutely no deodorization of the obtained hexamethyldisiloxane was observed.

EXAMPLE 2

In this example, the waste solution recovered from silylation was a hexamethyldisiloxane solution which contained 85% hexamethyldisiloxane, and as impurities 10% 1,4-dioxane, 1% dimethylaniline, 1% trimethylisobutoxysilane, and 3% other. 1,200 kg of such a solution, 15 kg concentrated hydrochloric acid, and 300 kg tap water were all placed in a 2 cubic meter reaction kettle, followed by stirring for 2 hours and then standing. After separation, the acidic lower aqueous layer was removed, and the upper liquid layer was repeatedly washed with 200 l tap water to neutrality. It was then transferred to a 1 cubic meter distillation kettle equipped with a packed column (diameter=30 cm, length=6 m), and the hexamethyldisiloxane was then distilled. Hexamethyldisiloxane having a purity of 99.0% or better was continuously distilled off (reflux ratio=5:1 to 10:1) as the fraction boiling at 99° C. cubic meter treatment kettle. Acid clay (K-500 from Nippon Kassei Hakudo Kabushiki Kaisha) was added to the treatment kettle at 1% based on the distillate present therein, and the temperature was then raised to 80° to 90° C. with stirring. At this point, the injection of nitrogen gas from the bottom of the kettle into the liquid was initiated at a rate of 1 cubic meter per hour. These conditions were maintained for 9 hours.

After cooling, the acid clay was continuously filtered from the hexamethyldisiloxane, which was then continuously passed through a column (diameter=10 cm, length=2 m) packed with 12 kg activated carbon (Kuraray Coal GL8/48, a granular activated carbon from Kuraray Chemical Kabushiki Kaisha). 950 kg of a purified, deodorized hexamethyldisiloxane was obtained by filtration across a 1 micron polypropylene cartridge-type filter.

What is claimed is:

1. A method for purifying impure hexamethyldisiloxane comprising as a major portion hexamethyldisiloxane and as a minor portion a mixture of low-boiling organic solvents, other organosilicon compounds, and odor-producing materials, said method comprising
   (A) first, treating the impure hexamethyldisiloxane with a condensation catalyst to convert the other organosilicon compounds to additional hexamethyldisiloxane;
   (B) second, washing the treated impure hexamethyldisiloxane from (A) with water;
   (C) third, separating a water phase from the washed, treated impure hexamethyldisiloxane;
   (D) fourth, distilling the washed, treated impure hexamethyldisiloxane to yield hexamethyldisiloxane of enhanced purity;
   (E) fifth, contacting the hexamethyldisiloxane of enhanced purity with acid clay at a temperature of greater than about 50° C.; and
   (F) finally, contacting the hexamethyldisiloxane of enhanced purity treated in (E) with activated carbon.

2. A method according to claim 1, wherein (A) further comprises adding water to the treating of the impure hexamethyldisiloxane with the condensation catalyst.

3. A method according to claim 1, wherein the condensation catalyst is selected from a group consisting of acidic compounds and basic compounds.

4. A method according to claim 3, wherein the acidic compounds are selected from a group consisting of hydrochloric acid, sulfuric acid, acetic acid, and paratoluenesulfonic acid.

5. A method according to claim 3, wherein the basic compounds are selected from a group consisting of sodium hydroxide, potassium hydroxide, and organic amines.

6. A method according to claim 1, wherein the condensation catalyst is present in a range from about 0.01 to 1.0 weight percent relative to the weight of the impure hexamethyldisiloxane.

7. A method according to claim 1, wherein treating the impure hexamethyldisiloxane with the condensation catalyst is effected at a temperature less than about 100° C.

8. A method according to claim 1, the acid clay is present at a concentration in a range from about 0.01 to 10 weight percent relative to the weight of the hexamethyldisiloxane of enhanced purity.

9. A method according to claim 1, wherein the contacting the acid clay with the hexamethyldisiloxane of enhanced purity is effected at a temperature in a range from about 50° to 98° C.

10. A method according to claim 1, wherein contact of the hexamethyldisiloxane of enhanced purity with activated carbon is effected at a temperature less than about 100° C.

11. A method according to claim 1, wherein the activated carbon is present at a concentration in a range from about 0.01 to 5.0 weight percent relative to the weight of the hexamethyldisiloxane of enhanced purity.

12. A method according to claim 1, wherein contacting the hexamethyldisiloxane of enhanced purity treated in (E) with activated carbon is carried out in a batch mode in which the activated carbon is filtered from the hexamethyldisiloxane after contact.

13. A method according to claim 1, wherein contacting the hexamethyldisiloxane of enhanced purity treated in (E) with activated carbon is carried out in a continuous mode in which the hexmethyldisiloxane is passed through a packed bed of activated carbon.

* * * * *